US00PP18171P2

(12) United States Plant Patent
Egger

(10) Patent No.: US PP18,171 P2
(45) Date of Patent: Oct. 30, 2007

(54) ***HEUCHERA* PLANT NAMED 'FANTASIA'**

(50) Latin Name: ***Heuchera* spp.**
Varietal Denomination: Fantasia

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 5 days.

(21) Appl. No.: 11/452,685

(22) Filed: Jun. 13, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Klarquist Sparkman, LLP

(57) ABSTRACT

A new and distinct hybrid of *Heuchera* plant characterized by spring and summer silver leaves with distinctive dark veins, bright bicolor hot pink/pink, wand type flowers on numerous flowering stems, a mounding habit and excellent vigor.

1 Drawing Sheet

Botanical denomination: *Heuchera* spp.
Variety designation: 'Fantasia'.

The present invention relates to a new and distinct cultivar of *Heuchera* hybrid and given the cultivar name of 'Fantasia'. *Heuchera* is in the family Saxifragaceae. *Heuchera* 'Fantasia' originated from a cross between *Heuchera* 24-1 (an unpatented, proprietary plant) as the seed parent, and *Heuchera* 42-1 (an unpatented, proprietary plant) as the pollen parent. Given its ornamental foliage and flower form, it is probable that *Heuchera sanguinea, H. americana,* and *H. micrantha* are in its parentage.

This new *Heuchera* is distinguished by:

1. Silver spring and summer leaves,
2. Bright bicolor hot pink/pink, wand type flowers on numerous flowering stems,
3. Mounding habit,
4. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The drawing shows a two-year-old plant of *Heuchera* 'Fantasia' growing in a two gallon container in the shade house in May in Canby, Oreg.

DETAILED PLANT DESCRIPTION

The following is a detailed description of the new *Heuchera* cultivar based on observations taken in May of a two-year-old specimen grown a two gallon container in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—17 cm tall from the ground to the top of the foliage and 40 cm wide.
*Habit.*—Mounding.
*Vigor.*—Excellent.
*Roots.*—Fibrous, freely branching, fine, and white in color, roots develop easily from cuttings.

Leaf:

*Type.*—Simple.
*Arrangement.*—Rosette.
*Shape.*—Broadly ovate.
*Lobing/division.*—5 main lobes, shallow and rounded, each notched 1 to 2 times.
*Venation.*—Palmate.
*Margins.*—Broadly crenate, glandular.
*Apex.*—Mucronulate.
*Base.*—Cordate, lobes strongly overlapping at the base, sometimes causing the leaf to pleat.
*Blade size.*—6 to 9 cm long and 5.7 to 8.6 cm wide.
*Surface texture.*—Top surface is glabrous, bottom has very short glands along main veins.
*Petiole description.*—9 to 15 cm long and 2 mm wide with the surface having numerous very short glandular hairs and occasional long glandular hairs, color is Greyed Orange 177A.
*Leaf color.*—Top side — In spring through fall the leaves are strongly silver Greyed Green 198C with the areas at the leaf edges and closely around the veins between Black 202A and Brown 200A. The veins near the leaf base are Greyed Red 178A.

Winter leaves are silver, Greyed Green 198C, with olive green, closest to Greyed Green 191A around the veins and at the margin. Bottom side — Maroon, closest to Red Purple 59A.

Inflorescence:

*Type.*—Thyrse, in a wand shape.

*Number of flowers.*—102 per thyrse.

*Number of thyrse in spring.*—30 in the first flush.

*Peduncle.*—With 0 to 1 cauline leaf, 30 to 40 cm tall and 3 mm wide at the base, between Brown 200A and Yellow Green 148A, with glandular hairs.

*Pedicel.*—Variable in length, Brown 200A, with glandular hairs.

*Bloom period.*—May and June in Canby, Oreg.

Flower bud:

*Size.*—2.5 mm wide and 4 mm long.

*Description.*—Glandular, ovoid, down facing.

*Color.*—Light pink, Red Purple 63C with hot pink tips, Red Purple 64A.

Flower:

*Type.*—Perfect, zyogomorphic.

*Shape.*—Campanulate.

*Size.*—5 mm long and 3 mm wide.

*Petal description.*—5, inconspicuous, inside the sepals, spatulate with a clawed base, tips acute, margin entire, back side with glandular hairs, top side glabrous, 2 mm long and 0.6 mm wide, light pink, Red Purple 63C on both sides.

*Calyx.*—Campanulate, 5 lobes, close together, divided ⅓ way to the base, glandular, tips acute, margin entire, 5 mm long and 3 mm wide.

*Calyx and overall flower color.*—Red Purple 63C to 63D with top ⅓ Red Purple 67A to 63A.

*Stamen description.*—5 in number, extruding from calyx, anthers sterile, no pollen produced, oval and about 0.5 mm long, Yellow White 158A, filaments 5.3 mm long, White 155D.

*Pistil description.*—Extruding from calyx, 6 mm long, White 155B overall, stigma is 2 parted, pink, Red Purple 63C.

*Fragrance.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm. long.

*Color.*—Black 202A.

Pest and disease tolerance: Excellent disease resistance to powdery mildew, the common problem of *Heuchera.* Susceptible to *Heuchera* rust and root weevils.

COMPARISON TO SIMILAR *HEUCHERA*

Compared to *Heuchera* 'Fandango' (U.S. Plant patent application Ser. No. 11/158,497), this new variety has less cut and ruffled leaves which are broader and much more heavily silvered.

Compared to *Heuchera* 'Autumn Haze' (U.S. Plant Pat. No. 12,160), *Heuchera* 'Fantasia' has wand type flowers and darker leaves that are more silver in color.

Compared to the seed parent, *Heuchera* 24-1 (an unpatented, proprietary plant), the new variety has larger, darker leaves and larger pink flowers.

Compared to the pollen parent, *Heuchera* 42-1 (an unpatented, proprietary plant), the new variety has larger flowers, darker leaves, and is heavily veiled rather than not veiled.

I claim:

1. A new and distinct hybrid of *Heuchera* plant as herein illustrated and described.

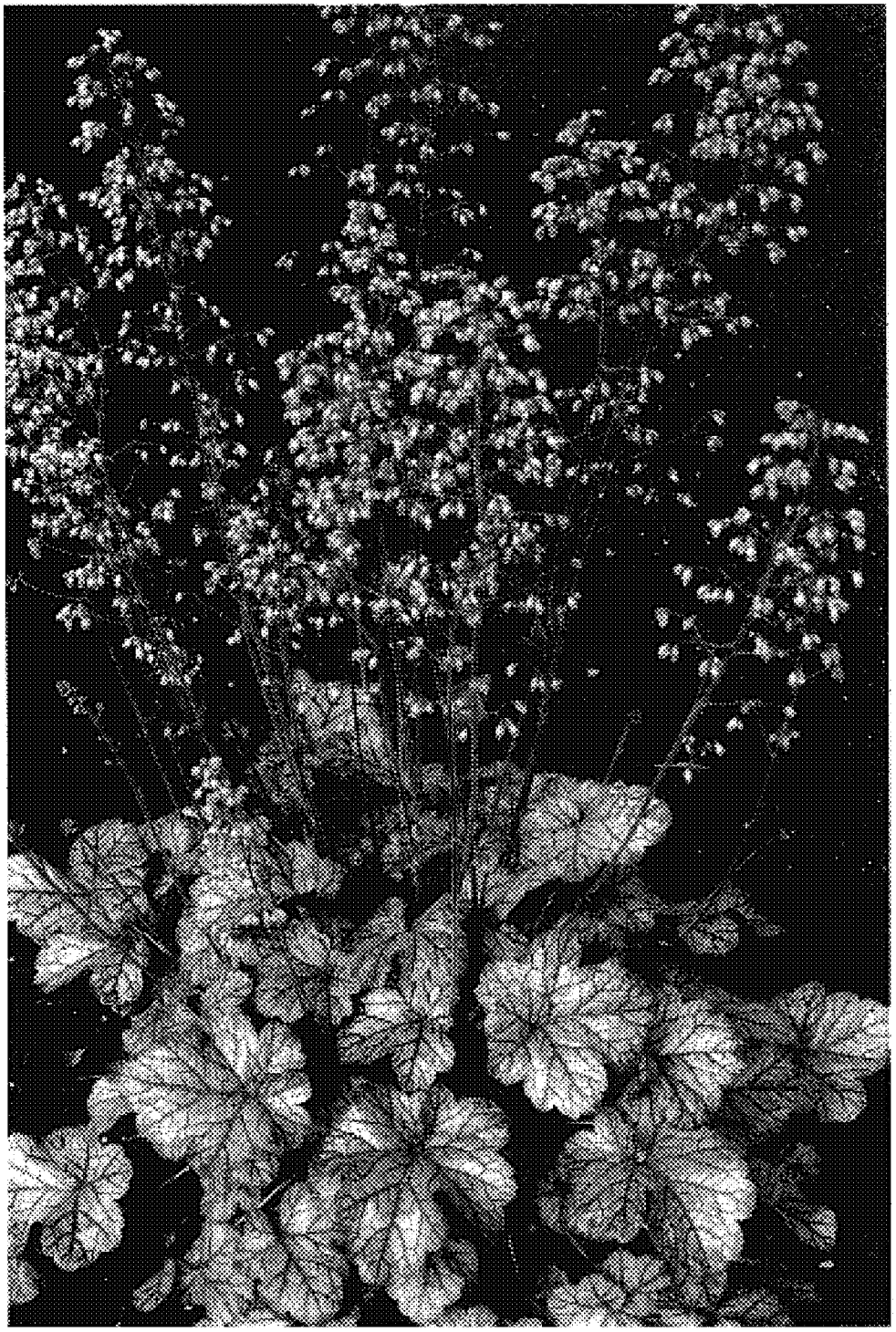

* * * * *